United States Patent [19]

Carr

[11] Patent Number: 4,624,273

[45] Date of Patent: Nov. 25, 1986

[54] PIGMENTED COMPOSITION

[75] Inventor: Raymond Carr, Devon, England

[73] Assignee: Atlas Pencil Company Limited, Devon, England

[21] Appl. No.: 670,922

[22] Filed: Nov. 13, 1984

[30] Foreign Application Priority Data

Nov. 11, 1983 [GB] United Kingdom ............... 8330201

[51] Int. Cl.$^4$ ............................................. A45D 40/26
[52] U.S. Cl. ................................................... 132/88.7
[58] Field of Search ............... 132/88.5, 88.7; 401/49, 401/96

[56] References Cited

U.S. PATENT DOCUMENTS

| 2,409,000 | 10/1946 | Rubenstein | 401/49 |
| 4,413,921 | 11/1983 | Fotiu | 401/49 |

FOREIGN PATENT DOCUMENTS

| 0025368 | 2/1980 | Japan | 401/49 |
| 0058067 | 4/1984 | Japan | 401/49 |
| 0059759 | 4/1984 | Japan | 401/49 |
| WO82/00444 | 2/1982 | World Int. Prop. O. | 401/49 |

OTHER PUBLICATIONS

Sagarin, Cosmetics/Technology, 1957, pp. 403–404, 615–616 & 617.

Primary Examiner—Gregory E. McNeill
Attorney, Agent, or Firm—Young & Thompson

[57] ABSTRACT

Cosmetic pencils having cores consisting of water-set mixtures of plaster of paris, mica or other laminar material and pigment or color are disclosed. The mixtures are between 30 wgt % and 75 wgt % plaster of paris. The pencils may be made either by pouring water-based slurries of the mixtures into hollow pencil cases, or by introducing pre-formed cores into two-part cases which are subsequently secured together. The pencils can be easily sharpened and may contain a wide range of additives such as preservatives and bacterioistats.

21 Claims, 1 Drawing Figure

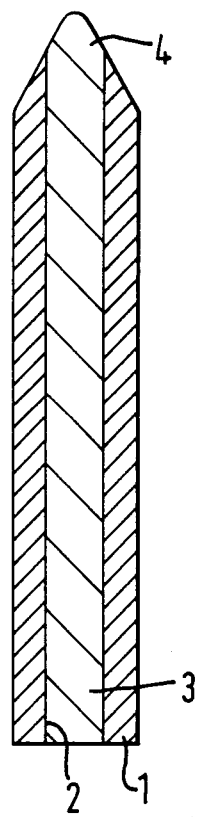

PIGMENTED COMPOSITION

BACKGROUND TO THE INVENTION

1. Field of the Invention

This invention relates to pigmented compositions, for example compositions suitable for forming the core of a cosmetic pencil.

2. Description of Prior Art

A known cosmetic powder pencil core consists of pigment or colouring material, an extender such as a clay for modifying the intensity of the pigment or colouring material, a modifier such as a clay or zinc stearate for modification of the structure or other properties of the core, and a binder comprising a gum or gum-like material.

BRIEF SUMMARY OF THE INVENTION

The present invention provides a composition comprising a pigment or colouring material, plaster of paris (calcium sulphate hemihydrate) and mica or other material having a laminar structure, the composition containing 30 to 75 wgt %, preferably 35 to 70 wgt % and, more preferably, at least 40 wgt % plaster of paris. Most preferably, the composition contains about 45 wgt % plaster of paris.

The amount of laminar material may be as low as 10 wgt % of the composition but is preferably at least 20 wgt % of the composition. The preferred upper limit to the amount of laminar material is 50 wgt % of the composition. The particle size of the laminar material is preferably in the range of from 5 μm to 100 μm and more preferably in the range of from 5 μm to 40 μm.

The composition may also contain additives or modification agents, for example emollients, fillers, extenders, preservatives, bacteriostats and accelerators or retarders for the setting of the plaster of paris component. Preferably, the total amount of additives or modification agents is no more than 5 wgt % of the composition.

Compositions according to the invention may include some calcium sulphate dihydrate or barium sulphate in the dry mix of ingredients, the preferred amount being up to 20 wgt % of the composition.

The pigment or colouring material advantageously comprises an opacifying agent such as titanium dioxide or bismuth oxychloride. The mica or laminar material may conveniently be coated with opacifying agent and/or be pre-mixed with the pigment or colouring material. Alternatively, one or all of the opacifying agent, the pigment or colouring material and the laminar material can be added as separate ingredients to the plaster of paris. The preferred level of pigment or colouring material in the composition is from 5 to 30 wgt % of the composition.

To form the dry composition into a pencil core, a portion of the dry composition is mixed with water, formed into a desired core shape, caused or allowed to set and then dried. Accelerating or retarding agents for plaster of paris may be added to the dry composition or the mixture. Typically, the dry composition is mixed with approximately twice its weight of water.

Instead of introducing the additives or modification agents mentioned above into the dry mix of ingredients, these additives or agents may be first disolved in water to form an aqueous solution in which the other dry ingredients are subsequently disolved.

In one procedure for making a cosmetic pencil, after mixing and before setting, the wet material in the form of a slurry is poured or pumped directly into preformed wooden pencil cases, comprising wooden cylinders each with a longitudinal cylindrical bore. The cases are conveniently held in an upright position with an open end of the bore uppermost. When no accelerator or retardant is used setting may be achieved by allowing the filled case to stand for approximately 20 minutes at room temperature. This period may be lengthened to about 2 hours or shortened to about 3 minutes by use of a suitable retardant or accelerator. The set composition may then be dried at an elevated temperature of, say, 35° to 60° C. for a period of, for example, 24, 48 or 72 hours. Otherwise, drying may be achieved by allowing the filled cases to stand at room temperature for an appropriate time period, or by freeze or vacuum drying. During the drying process water from the mixture evaporates through the tip of the core exposed by the case and also through the wooden case material which is sufficiently porous to allow such evaporation. In the setting process, the calcium sulphate hemihydrate is converted to calcium sulphate dihydrate and the set composition therefore contains a stoichiometric amount of water. Apart from this water of crystallisation, the set compositions will contain little or no water.

In another procedure, the wet composition is moulded and set into rod-shaped pencil cores which are subsequently introduced into a two-part wooden block having a plurality of recesses which are opened longitudinally for introduction of the cores when the block parts are separated. After fitting of the cores to one block part, the two parts are united, the parts secured together and the block cut and shaped into a plurality of pencils. The cores are then allowed to dry.

It has been found that the cores of cosmetic pencils made in accordance with the present invention can have excellent adhesion to their cases.

After drying, the pencils formed by either procedure are sharpened at one end to form and expose a conical tip of the core.

The composition of the invention has the advantages of inexpensiveness and simplicity compared with the known core composition. The finished pencil has an improved appearance compared with known cosmetic pencils and can contain a much wider range of additive materials, for example emollients, preservatives and bacteriostats. The pay-off properties of the pencils are also good.

BRIEF DESCRIPTION OF THE DRAWING

The sole FIGURE of the drawing of this specification shows a cosmetic powder pencil made in accordance with one aspect of the present invention.

DETAILED DESCRIPTION

The pencil comprises a cylindrical wooden pencil case 1 having a longitudinal cylindrical bore 2 into which has been poured or pumped a mixture of a composition according to the invention and water, the mixture having subsequently set to form a core 3 of the pencil. The core is about 12 cm long and about 6.9 mm in diameter. One end of the core 3 has been sharpened into a conical tip 4.

In a modified procedure, the tip 4 can be formed integrally with the remainder of the core 3 by moulding.

In a further modification, two pencils are formed simultaneously in a case of twice the length shown in the drawings which is subsequently cut into two equal-length parts.

Examples will now be given of compositions according to the invention:

EXAMPLE 1

Composition for Dark Blue Cosmetic Pencil

|  |  | wgt % |
|---|---|---|
| Plaster of paris |  | 64.6 |
| Titanium dioxide | } as TiO$_2$ coated mica | 6.5 |
| Mica |  | 18.5 |
| Ferric ferrocyanide |  | 10.0 |
| Methylparahydroxybenzoate |  | 0.2 |
| Propylparahydroxybenzoate | } Preservatives | 0.1 |
| Sodium dehydroacetate |  | 0.1 |
|  |  | 100.0 |

EXAMPLE 2

Composition for Light Blue Cosmetic Pencil

|  |  | wgt % |
|---|---|---|
| Plaster of paris |  | 49.6 |
| Titanium dioxide | } as TiO$_2$ coated mica | 13.6 |
| Mica |  | 26.4 |
| Ferric ferrocyanide |  | 10.0 |
| Methylparahydroxybenzoate |  | 0.2 |
| Propylparahydroxybenzoate | } Preservatives | 0.1 |
| Sodium dehydroacetate |  | 0.1 |
|  |  | 100.0 |

EXAMPLE 3

Composition for Green Cosmetic Pencil

|  |  | wgt % |  |
|---|---|---|---|
| Plaster of paris |  | 49.6 |  |
| Titanium dioxide | } as TiO$_2$ coated mica | 23.0 |  |
| Mica |  | 23.0 | } Pre- mixed |
| Iron oxide |  | 3.0 |  |
| Ferric ferrocyanide |  | 1.0 |  |
| Methylparahydroxybenzoate | } Preservatives | 0.2 |  |
| Propylparahydroxybenzoate |  | 0.1 |  |
| Sodium Dehydroacetate |  | 0.1 |  |
|  |  | 100.0 |  |

In each Example, the ingredients listed above were thoroughly mixed together and then mixed with approximately twice their weight of water. The wet mixture could then be used in the manufacture of cosmetic pencils in a manner described hereinbefore.

For use in Examples 4 to 42 which follow, the following aqueous bacteriocide and fungicide solution was prepared;

2 parts by volume of a 1% sodium dehydroacetate solution in deionised water 4 parts by volume of 1% Germall 115 solution in deionised water 29 parts by volume of deionised water Dry mixtures as specified in Examples 4 to 35 were then made up and 200 g portions of the mixtures were mixed with the volumes of the bacteriocide and fungicide solution stated in the individual examples. The mixtures were stirred gently to avoid aeration, sieved and then injected by means of an injection gun into empty wooden pencil cases in the form of hollow cylinders of 6.90 mm internal diameter and mm in length. The total time from mixing to injection did not exceed 12 minutes. Within 12 minutes of injection the pencils cores had solidified. The pencils were then transferred to a drying oven for a period of between 48 and 72 hours. After drying, one end of each pencil was sharpened with a pencil-sharpener to produce a finished make-up pencil.

In the following examples the figures in parentheses after certain pigments or colouring materials indicate that those materials contain mica in the indicated amounts by weight.

EXAMPLE 4

Composition for Highlighter Pencil

|  |  | wgt % |
|---|---|---|
| 12.5 kg | Superfine casting plaster of paris | 50.0 |
| 12.0 kg | Soloron Silver (70%) | 48.0 |
| 0.5000 kg | Ariabel Umber | 2.0 |
| Mica content of mixture |  | 33.6 |
| Pigment content of mixture |  | 16.4 |

200 g of the mixture was mixed with 275 cm$^3$ of bacteriocide and fungicide solution.

EXAMPLE 5

Composition for Golden Bronze Pencil

|  |  | wgt % |
|---|---|---|
| 2.00 kg | Superfine casting plaster of paris | 50.0 |
| 2.00 kg | Cloisonne Golden Bronze (62 to 68%) | 50.0 |
| Mica content of mixture |  | 31.0 to 34.0 |
| Pigment content of mixture |  | 16.0 to 19.0 |

200 g of the mixture was mixed with 290 cm$^3$ of bacteriocide and fungicide solution.

EXAMPLE 6

Composition for Green Pencil

|  |  | wgt % |
|---|---|---|
| 13.75 kg | Superfine casting plaster of paris | 55.0 |
| 11.25 kg | Cloisonne Super Green (44 to 48%) | 45.0 |
| Mica content of mixture |  | 19.8 to 21.6 |
| Pigment content of mixture |  | 23.4 to 25.2 |

200 g of the mixture was mixed with 225 cm$^3$ of bacteriocide and fungicide solution.

EXAMPLE 7

Composition for Silver Grey Pencil

|  |  | wgt % |
|---|---|---|
| 12.50 kg | Superfine casting plaster of paris | 50.0 |
| 10.00 kg | Soloron Silver (70%) | 40.0 |
| 2.50 kg | Black 300401 | 10.0 |
| Mica content of mixture |  | 28.0 |
| Pigment content of mixture |  | 22.0 |

200 g of the mixture was mixed with 350 cm$^3$ of bacteriocide and fungicide solution.

EXAMPLE 8

Composition for Blue Pencil

| | | wgt % |
|---|---|---|
| 11.875 kg | Superfine casting plaster of paris | 47.50 |
| 11.875 kg | Duochrome BR (55–62%) | 47.50 |
| 1.250 kg | 300308 Ariabel Blue | 5.00 |
| Mica content of mixture | | 26.12 to 29.44 |
| Pigment content of mixture | | 23.06 to 26.38 |

200 g of the mixture was mixed with cm³ of bacteriocide and fungicide solution.

EXAMPLE 9

Composition for Dusty Pink Pencil

| | | wgt % |
|---|---|---|
| 13.75 kg | Superfine casting plaster of paris | 55.00 |
| 10.16 kg | Soloron Silver (70%) | 40.64 |
| 0.62 kg | Carmine 1275 | 2.48 |
| 0.38 kg | Black 300401 | 1.52 |
| 0.09 kg | Blue 300308 | 0.36 |
| Mica content of mixture | | 28.45 |
| Pigment content of mixture | | 16.55 |

200 g of the mixture was mixed with 300 cm³ of bacteriocide and fungicide solution.

EXAMPLE 10

Composition for Green Pencil

| | | wgt % |
|---|---|---|
| 13.75 kg | Superfine casting plaster of paris | 55.0 |
| 9.75 kg | Cloisonne Nu Antique Gold | 39.0 |
| 1.25 kg | Black iron oxide 300401 | 5.0 |
| 0.25 kg | Ariabel Blue 300308 | 1.0 |
| Mica content of mixture | | 19.89 to 22.23 |
| Pigment content of mixture | | 22.77 to 25.11 |

200 g of the mixture was mixed with 250 cm³ of bacteriocide and fungicide solution.

EXAMPLE 11

Composition for Mulberry Pencil

| | | wgt % |
|---|---|---|
| 13.25 kg | Superfine casting plaster of paris | 53.00 |
| 5.00 kg | Soloron Silver (70%) | 20.00 |
| 5.35 kg | Cloisonne Nu Antique Rouge Flambe | 21.40 |
| 0.60 kg | Black 300401 | 2.40 |
| 0.80 kg | Red 300318 | 3.20 |
| Mica content of mixture | | 24.49 to 25.77 |
| Pigment content of mixture | | 21.23 to 22.51 |

200 g of the mixture was mixed with 280 cm³ of bacteriocide and fungicide solution.

EXAMPLE 12

Composition for Blue Pencil

| | | wgt % |
|---|---|---|
| 1.70 kg | Superfine casting plaster of paris | 42.50 |
| 2.08 kg | Duochrome BR (55 to 62%) | 52.00 |
| 0.22 kg | 300308 Blue | 5.50 |
| Mica content of mixture | | 28.6 to 32.24 |
| Pigment content of mixture | | 25.26 to 28.9 |

200 g of the mixture was mixed with 270 cm³ of bacteriocide and fungicide solution.

EXAMPLE 13

Composition for Punk Pink Pencil

| | | wgt % |
|---|---|---|
| 2.00 k | Superfine casting plaster of paris | 50.0 |
| 2.0 kg | Duochrome RB (48 to 54%) | 50.0 |
| Mica content of mixture | | 24.0 to 27.0 |
| Pigment content of mixture | | 23.0 to 26.0 |

200 g of the mixture was mixed with 250 cm³ of bacteriocide and fungicide solution.

EXAMPLE 14

Composition for Silver Grey Pencil

| | | wgt % |
|---|---|---|
| 1.80 kg | Superfine casting plaster of paris | 45.0 |
| 1.80 kg | Soloron Silver (70%) | 45.0 |
| .40 kg | Black 300401 | 10.0 |
| Mica content of mixture | | 31.5 |
| Pigment content of mixture | | 23.5 |

200 g of the mixture was mixed with 350 cm³ of bacteriocide and fungicide solution.

EXAMPLE 15

Composition for Gold Pencil

| | | wgt % |
|---|---|---|
| 1.80 kg | Superfine casting plaster of paris | 45.0 |
| 2.20 kg | Cloisonne Golden Bronze (62 to 68%) | 55.0 |
| Mica content of mixture | | 34.1 to 37.4 |
| Pigment content of mixture | | 17.6 to 20.9 |

200 g of the mixture was mixed with 300 cm³ of bacteriocide and fungicide solution.

EXAMPLE 16

Composition for Antique Bronze Pencil

| | | wgt % |
|---|---|---|
| 1.90 kg | Superfine casting plaster of paris | 47.50 |
| 1.80 kg | Cloisonne Nu Antique Gold (51 to 57%) | 45.50 |
| 0.24 kg | Black 300401 | 6.00 |
| .40 kg | Blue 300308 | 1.00 |
| Mica content of mixture | | 23.21 to 25.94 |
| Pigment content of mixture | | 26.56 to 29.29 |

200 g of the mixture was mixed with 270 cm³ of bacteriocide and fungicide solution.

EXAMPLE 17

Composition for Highlighter Pencil

| | | wgt % |
|---|---|---|
| 1.80 kg | Superfine casting plaster of paris | 45.0 |
| 2.12 kg | Soloron Silver (70%) | 53.0 |

|  |  | wgt % |
| --- | --- | --- |
| 0.08 kg | Umber 300403 | 2.0 |
| Mica content of mixture | | 37.1 |
| Pigment content of mixture | | 17.9 |

200 g of the mixture was mixed with 360 cm³ of bacteriocide and fungicide solution.

EXAMPLE 18

Composition for Blue Highlighter Pencil

|  |  | Wgt % |
| --- | --- | --- |
| 1.80 kg | Superfine casting plaster of paris | 45.0 |
| 2.20 kg | Duochrome YB (48 to 54%) | 55.0 |
| Mica content of mixture | | 26.4 to 29.7 |
| Pigment content of mixture | | 25.3 to 28.6 |

200 g of the mixture was mixed with 250 cm³ of bacteriocide and fungicide solution.

EXAMPLE 19

Composition for Apple Cordial Pencil

|  |  | Wgt % |
| --- | --- | --- |
| 1.80 kg | Superfine casting plaster of paris | 45.0 |
| 2.20 kg | Duochrome GY (58 to 64%) | 55.0 |
| Mica content of mixture | | 31.9 to 35.2 |
| Pigment content of mixture | | 19.8 to 23.1 |

200 g of the mixture was mixed with 250 cm³ of bacteriocide and fungicide solution.

EXAMPLE 20

Composition for Sapphire Pencil

|  |  | Wgt % |
| --- | --- | --- |
| 1.80 kg | Superfine casting plaster of paris | 45.00 |
| 1.60 kg | Cloisonne Blue (48 to 54%) | 40.00 |
| 0.38 kg | RS 5 Ultra Blue | 9.50 |
| 0.22 kg | Soloron Silver Sparkle (70%) | 5.50 |
| Mica content of mixture | | 23.05 to 25.45 |
| Pigment content of mixture | | 29.55 to 31.95 |

200 g of the mixture was mixed with 250 cm³ of bacteriocide and fungicide solution.

EXAMPLE 21

Composition for Sky Blue Pencil

|  |  | Wgt % |
| --- | --- | --- |
| 1.80 kg | Superfine casting plaster of paris | 45.00 |
| 1.152 kg | Soloron Silver (70%) | 28.80 |
| 0.86 kg | Timiron MP45 (80%) | 21.50 |
| 0.18 kg | RS 5 Ultra Blue | 4.50 |
| 0.008 kg | Ariabel Blue 300 | 0.20 |
| Mica content of mixture | | 38.65 |
| Pigment content of mixture | | 16.35 |

EXAMPLE 22

Composition for Blue Mist Pencil

|  |  | Wgt % |
| --- | --- | --- |
| 1.80 kg | Superfine casting plaster of paris | 45.0 |
| 2.20 kg | Duochrome GB (58 to 64%) | 55.0 |
| Mica content of mixture | | 31.9 to 35.2 |
| Pigment content of mixture | | 19.8 to 23.1 |

200 g of the mixture was mixed with 230 cm³ of bacteriocide and fungicide solution.

EXAMPLE 23

Composition for Jade Pencil

|  |  | Wgt % |
| --- | --- | --- |
| 1.80 kg | Superfine casting plaster of paris | 45.0 |
| 1.84 kg | Soloron Blue Green (45%) | 46.0 |
| 0.24 kg | Ariabel Green | 6.0 |
| 0.12 kg | Soloron Silver (70%) | 3.0 |
| Mica content of mixture | | 22.8 |
| Pigment content of mixture | | 32.2 |

200 g of the mixture was mixed with 300 cm³ of bacteriocide and fungicide solution.

EXAMPLE 24

Composition for Mocca Pencil

|  |  | wgt % |
| --- | --- | --- |
| 1.80 kg | Superfine casting plaster of paris | 45.0 |
| 1.32 kg | Soloron Silver (70%) | 33.0 |
| 0.40 kg | Ariabel Yellow 300407 | 10.0 |
| 0.32 kg | Ariabel Umber 300403 | 8.0 |
| 0.16 kg | Ariabel Black 300401 | 4.0 |
| Mica content of mixture | | 23.1 |
| Pigment content of mixture | | 31.9 |

200 g of the mixture was mixed with 340 cm³ of bacteriocide and fungicide solution.

EXAMPLE 25

Composition for Khaki Pencil

|  |  | wgt % |
| --- | --- | --- |
| 1.80 kg | Superfine casting plaster of paris | 45.0 |
| 1.80 kg | Cloisonne Nu Antique Gold (51 to 57%) | 45.0 |
| 0.20 kg | Black 300401 | 5.0 |
| 0.04 kg | Blue 300308 | 1.0 |
| 0.16 kg | Soloron Silver (70%) | 4.0 |
| Mica content of mixture | | 25.75 to 28.45 |
| Pigment content of mixture | | 26.55 to 29.25 |

200 g of the mixture was mixed with 295 cm³ of bacteriocide and fungicide solution.

EXAMPLE 26

Composition for Baby Blue Pencil

|  |  | wgt % |
| --- | --- | --- |
| 1.80 kg | Superfine casting plaster of paris | 45.0 |
| 1.08 kg | Cloisonne Blue (48–54) | 27.0 |
| 0.72 kg | Soloron Silver (70) | 18.0 |
| 0.36 kg | 4500 Chromalite Blue | 9.0 |
| 0.004 kg | Blue 300308 | 1.0 |

-continued

| | wgt % |
|---|---|
| Mica content of mixture | 30.06 to 32.31 |
| Pigment content of mixture | 22.69 to 24.94 |

200 g of the mixture was mixed with 300 cm³ of bacteriocide and fungicide solution.

EXAMPLE 27

Composition for Lilac Mist Pencil

| | | wgt % |
|---|---|---|
| 1.80 kg | Superfine casting plaster of paris | 45.0 |
| 1.64 kg | Soloron Silver (70%) | 41.0 |
| 0.40 kg | Duochrome BR (55 to 62%) | 10.0 |
| 0.08 kg | Carmine | 2.0 |
| 0.04 kg | Black 300401 | 1.0 |
| 0.04 kg | Blue 300308 | 1.0 |
| Mica content of mixture | | 34.2 to 34.9 |
| Pigment content of mixture | | 20.1 to 20.8 |

200 g of the mixture was mixed with 330 cm³ of bacteriocide and fungicide solution.

EXAMPLE 28

Composition for Nearly Pink Pencil

| | | Wgt % |
|---|---|---|
| 1.80 kg | Superfine casting plaster of paris | 45.0 |
| 0.92 kg | Soloron Silver (70%) | 23.0 |
| 0.80 kg | Cloisonne Golden Bronze (62 to 68%) | 20.0 |
| 0.20 kg | Timica Copper (51 to 57%) | 5.0 |
| 0.28 kg | Duochrome RY (61 to 67%) | 7.0 |
| Mica content of mixture | | 35.32 to 37.24 |
| Pigment content of mixture | | 17.76 to 19.68 |

200 g of the mixture was mixed with 320 cm³ of bacteriocide and fungicide solution.

EXAMPLE 29

Composition for Apricot Frost Pencil

| | | wgt % |
|---|---|---|
| 1.80 kg | Superfine casting plaster of paris | 45.0 |
| 1.16 kg | Coloron Bright Gold (59%) | 29.0 |
| 0.88 kg | Soloron Silver (70%) | 22.0 |
| 0.08 kg | Cloisonne Golden Bronze (62 to 68%) | 2.0 |
| 0.08 kg | Ariabel Sienna 300406 | 2.0 |
| Mica content of mixture | | 33.75 to 33.87 |
| Pigment content of mixture | | 21.13 to 21.25 |

200 g of the mixture was mixed with 330 cm³ of bacteriocide and fungicide solution.

EXAMPLE 30

Composition for Brick Red Pencil

| | | Wgt % |
|---|---|---|
| 1.80 kg | Superfine casting plaster of paris | 45.0 |
| 2.20 kg | Cloisonne Rouge Flambe (49 to 55%) | 55.0 |
| Mica content of mixture | | 26.95 to 30.25 |
| Pigment content of mixture | | 24.75 to 28.05 |

200 g of the mixture was mixed with 270 cm³ bacteriocide and fungicide solution.

EXAMPLE 31

Composition for Stormy Black/Blue Pencil

| | | wgt % |
|---|---|---|
| 1.80 kg | Superfine casting plaster of paris | 40.0 |
| 1.40 kg | MP155 Blue (49%) | 35.0 |
| 0.60 kg | Black | 15.0 |
| 0.20 kg | Blue | 5.0 |
| Mica content of mixture | | 17.15 |
| Pigment content of mixture | | 37.85 |

100 g of the mixture was mixed with 290 cm³ bacteriocide and fungicide solution.

EXAMPLE 32

Composition for Twilight Pencil

| | | wgt % |
|---|---|---|
| 1.92 kg | Superfine casting plaster of paris | 48.0 |
| 1.60 kg | Woloron Silver (70%) | 40.0 |
| 0.40 kg | Black | 10.0 |
| 0.08 kg | Red 300418 | 2.0 |
| Mica content of mixture | | 28.0 |
| Pigment content of mixture | | 24.0 |

200 g of the mixture was mixed with 300 cm³ bacteriocide and fungicide solution.

EXAMPLE 33

Composition for Earth Glow Pencil

| | | wgt % |
|---|---|---|
| 1.80 kg | Superfine casting plaster of paris | 45.0 |
| 1.28 kg | MP127 Timiron Gold (57%) | 32.0 |
| 0.40 kg | Soloron Silver (70%) | 10.0 |
| 0.40 kg | Ariabel Umber | 10.0 |
| 0.02 kg | Black | 3.0 |
| Mica content of mixture | | 25.24 |
| Pigment content of mixture | | 29.76 |

200 g of the mixtures was mixed with 300 cm³ bacteriocide and fungicide solution.

EXAMPLE 34

Composition for Sunset Pencil

| | | wgt % |
|---|---|---|
| 1.80 kg | Superfine casting plaster of paris | 45.0 |
| 2.20 kg | Timica Copper (51 to 57%) | 55.0 |
| Mica content of mixture | | 28.05 to 31.35 |
| Pigment content of mixture | | 23.65 to 26.95 |

200 g of the mixture was mixed with 250 cm³ bacteriocide and fungicide solution.

EXAMPLE 35

Composition for Peacock Pencil

| | | wgt % |
|---|---|---|
| 2.00 kg | Superfine casting plaster of paris | 50.0 |
| 1.80 kg | Duochrome RB (48 to 54%) | 45.0 |
| 0.20 kg | Ariabel Blue | 5.0 |
| Mica content of mixture | | 21.6 to 24.3 |
| Pigment content of mixture | | 25.7 to 28.4 |

200 g of the mixture was mixed with 240 cm³ bacteriocide and fungicide solution.

EXAMPLE 36

Composition for Silver Pencil

|  | wgt % |
|---|---|
| Superfine casting plaster of paris | 30.0 |
| Soloron Silver (70%) | 69.0 |
| Black Iron Oxide | 1.0 |
| Mica content of mixture | 48.3 |
| Pigment content of mixture | 21.7 |

200 g of the mixture was mixed with 450 cm³ of bacteriocide and fungicide solution.

EXAMPLE 37

Composition for Silver Pencil

|  | wgt % |
|---|---|
| Superfine casting plaster of paris | 35.0 |
| Soloron Silver (70%) | 64.0 |
| Red Iron Oxide | 1.0 |
| Mica content of mixture | 44.8 |
| Pigment content of mixture | 20.2 |

200 g of the mixture was mixed with 475 cm³ of bacteriocide and fungicide solution.

EXAMPLE 38

Composition for Silver Pencil

|  | wgt % |
|---|---|
| Superfine casting plaster of paris | 40.0 |
| Soloron Silver (70%) | 60.0 |
| Mica content of mixture | 42.0 |
| Pigment content of mixture | 18.0 |

200 g of the mixture was mixed with 400 cm³ of bacteriocide and fungicide solution.

EXAMPLE 39

Composition for Silver Pencil

|  | wgt % |
|---|---|
| Superfine casting plaster of paris | 55.00 |
| Soloron Silver (70%) | 45.00 |
| Mica content of mixture | 31.50 |
| Pigment content of mixture | 13.50 |

200 g of the mixture was mixed with 325 cm³ of bacteriocide and fungicide solution.

EXAMPLE 40

Composition for Silver Pencil

|  | wgt % |
|---|---|
| Superfine casting plaster of paris | 60.00 |
| Soloron Silver (70%) | 39.00 |
| Red Oxide | 1.00 |
| Mica content of mixture | 27.30 |
| Pigment content of mixture | 12.70 |

200 g of the mixture was mixed with 300 cm³ of bacteriocide and fungicide solution.

EXAMPLE 41

Composition for Silver Pencil

|  | wgt % |
|---|---|
| Superfine casting plaster of paris | 65.00 |
| Soloron Silver (70%) | 34.00 |
| Red Iron Oxide | 1.00 |
| Mica content of mixture | 23.80 |
| Pigment content of mixture | 11.20 |

200 g of the mixture was mixed with 300 cm³ of bacteriocide and fungicide solution.

EXAMPLE 42

Composition for Silver Pencil

|  | wgt % |
|---|---|
| Superfine casting plaster of paris | 70.0 |
| Soloron Silver (70%) | 30.0 |
| Mica content of mixture | 21.0 |
| Pigment content of mixture | 9.0 |

200 g of the mixture was mixed with 275 cm³ of bacteriocide and fungicide solution.

I claim:

1. A pigmented or coloured composition which when mixed with water forms a set product adapted to be transferred to the skin as a cosmetic, the composition comprising a pigment or colouring material, plaster of paris and a material having a laminar structure, the composition containing from about 30 to about 75 wgt % plaster of paris.

2. The composition of claim 1, containing from about 35 to about 70 wgt % plaster of paris.

3. The composition of claim 1, containing from about 40 to about 70 wgt % plaster of paris.

4. The composition of claim 1, containing about 45 wgt % plaster of paris.

5. The composition of claim 1, containing at least about 10 wgt % material having a laminar structure.

6. The composition of claim 1, containing at least about 20 wgt % material having a laminar structure.

7. The composition of claim 1, containing no more than about 50 wgt % material having a laminar structure.

8. The composition of claim 1, wherein said material having a laminar structure is mica.

9. The composition of claim 1, wherein the particle size of said laminated material is in the range of from about 5 μm to about 10 μm.

10. The composition of claim 1, wherein the particle size of said laminar material is in the range of from about 5 μm to about 40 μm.

11. The composition of claim 1, containing from about 5 to about 30 wgt % pigment or colouring material.

12. The composition of claim 1, further comprising up to about 20 wgt % calcium sulphate dihydrate and/or barium sulphate.

13. The composition of claim 1, further comprising at least one additive material selected from emollients, fillers, extenders, preservatives, bacterioistats and accelerating and retarding agents for setting of plaster of paris.

14. The composition of claim 13, wherein the total amount of said additive material is less than about 5 wgt % of the composition.

15. The composition of claim 1, wherein said pigment or colouring material comprises an opacifying agent.

16. The composition of claim 15, wherein said material having a laminar structure is pre-coated with said opacifying agent before combination with the remainder of the composition.

17. The set product of a mixture of water and a composition according to claim 1.

18. A cosmetic pencil having a core comprising a set product as claimed in claim 17.

19. A method of making a cosmetic pencil, comprising the steps of forming a mixture of water and a pigmented composition as claimed in claim 1 into a pencil core, causing or allowing the mixture to set, assembling the set mixture with first and second pencil case parts and securing the parts together to form the pencil.

20. A method of making a cosmetic pencil, comprising the steps of forming a mixture of water and a pigmented composition as claimed in claim 1, introducing the mixture into a pre-formed pencil case and causing or allowing the mixture to set in the case to form the pencil.

21. The method of claim 20, further comprising the step of sharpening one end of the pencil.

* * * * *